(12) United States Patent
Schiffler

(10) Patent No.: US 8,531,653 B2
(45) Date of Patent: Sep. 10, 2013

(54) APPARATUS FOR THE ANALYSIS OF A FLUID

(75) Inventor: Ingo Schiffler, Freiburg (DE)

(73) Assignee: Sick AG, Waldkirch (DE)

( * ) Notice: Subject to any disclaimer, the term of this patent is extended or adjusted under 35 U.S.C. 154(b) by 104 days.

(21) Appl. No.: 13/181,571

(22) Filed: Jul. 13, 2011

(65) Prior Publication Data

US 2012/0033203 A1 Feb. 9, 2012

(30) Foreign Application Priority Data

Aug. 4, 2010 (EP) ..................................... 10171905

(51) Int. Cl.
*G01N 21/00* (2006.01)
(52) U.S. Cl.
USPC ........................................................... 356/72
(58) Field of Classification Search
USPC ........................................................... 356/72
See application file for complete search history.

(56) References Cited

U.S. PATENT DOCUMENTS

| | | |
|---|---|---|
| 5,404,228 A | 4/1995 | McGowan |
| 2006/0176484 A1* | 8/2006 | Steenhoek et al. ............ 356/413 |

FOREIGN PATENT DOCUMENTS

| | | |
|---|---|---|
| EP | 0 318 752 A2 | 6/1989 |
| WO | 2009/155459 A2 | 12/2009 |

OTHER PUBLICATIONS

Sick Maihak GmbH, "GM35 In-Situ Gas Analyzer: Multi-Component Analyzer for CO, CO2 and H2O as well as for Temperature and Pressure". 2009, pp. 1-4, XP-002615429, http://www.sick.fi/sickmaihak/product/categories/gasanalysis/gm35/en.toolboxpar.0011.file.tmp/PI_GM35_en_8009253.pdf.
Extended European Search Report issued on Jan. 24, 2011, in priority European Application No. 10171905.2.

\* cited by examiner

*Primary Examiner* — Tarifur Chowdhury
*Assistant Examiner* — Abdullahi Nur
(74) *Attorney, Agent, or Firm* — Nath, Goldberg & Meyer; Jerald L. Meyer; Scott C. Langford

(57) ABSTRACT

An apparatus for the analysis of a fluid in a line or in a container, having an optoelectronic apparatus, including: at least two housing parts having housing flanges for flanging to a wall of the line or of the container so that the housing parts are disposed opposite one another; a light transmitter and a light receiver which define an optical measurement path between them within the line or the container; and an evaluation unit, the apparatus further having a temperature measurement apparatus and/or a pressure measuring apparatus, wherein, the temperature measuring apparatus is held extending parallel to the optical measurement path within the line or the container via a spacer or a dynamic pressure pipe of the pressure measuring apparatus and the spacer or the dynamic pressure pipe is fastened to an intermediate flange which can be inserted between one of the housing flanges and the wall.

5 Claims, 1 Drawing Sheet

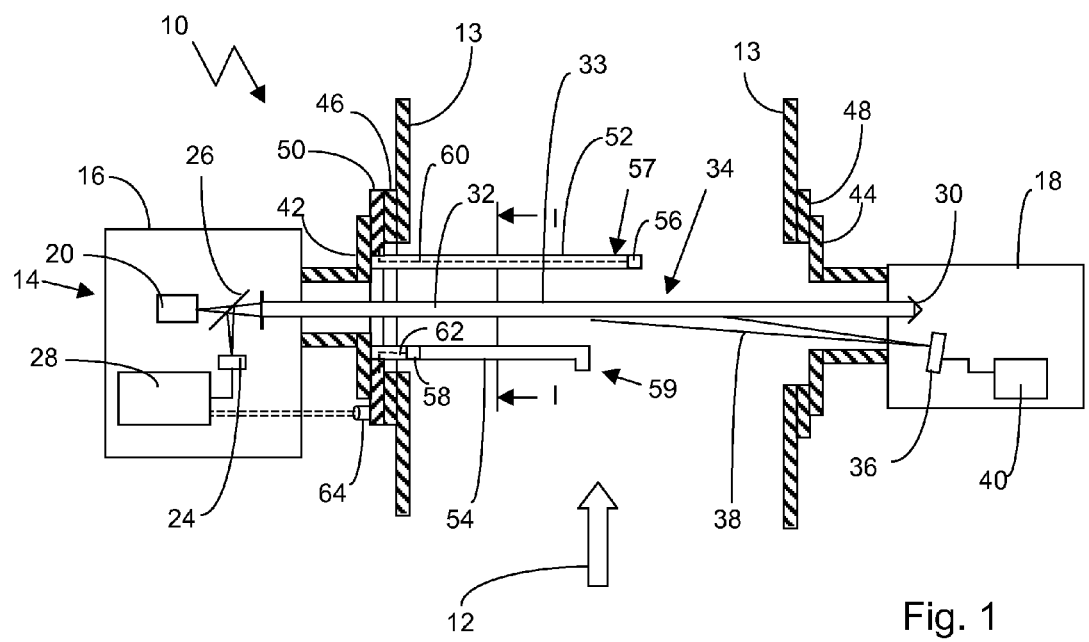
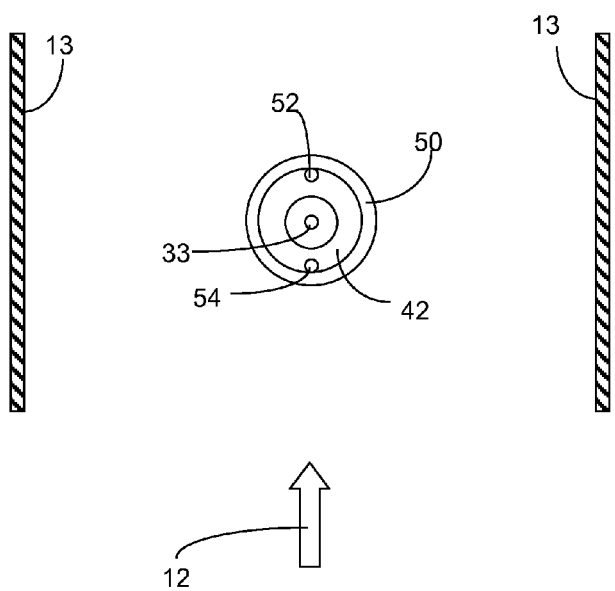

APPARATUS FOR THE ANALYSIS OF A FLUID

The invention relates to an apparatus for the analysis of a fluid in a line or in a container, having an optoelectronic apparatus for the optical analysis.

Such apparatus are, for example, optical spectrometers, visibility measuring devices, in situ gas analyzers and the like. Specific gas proportions, e.g. hydrogen sulfide, carbon monoxide, SO2, NH3, NO NO2, HCl, HF, or the like, are measured by means of optical transmission or light scattering using such apparatus. Fields of application are, for example, emission measurements of industrial plants in which the exhaust gases have to be monitored with respect to their content of specific molecular compounds. The concentration of the gas proportions is therefore usually determined. With most optical gas measuring devices, the pressure and the temperature of the gas to be measured has to be known to be able to calculate the correct concentration since the number of the molecules located in the measurement path depends on these parameters (gas law). In addition, these data are needed in some evaluation processes for the correct function of the algorithms.

Various possibilities are known for detecting pressure and temperature in such applications.

In an industrial plant, the pressure value and the temperature value are frequently provided at a number of positions. However, the values are usually not determined with sufficient precision. In addition, the measurement points are not located at the site of the gas analysis so that further substantial lacks of accuracy result.

It is in particular known to provide additional sensors at the site of the gas analysis. These additional sensors cause very high costs of which only a fraction is caused by the actual sensors; the main portion is rather caused by their installation, above all by the required welding in of additional flanges. This is further disadvantageous since the operator of an industrial plant always endeavors to have as few points of access in the plant since such "holes" always cause additional costs.

It is further known to determine the measurement of the temperature and/or of the pressure by the optical measuring process itself. The determination by the measuring process is only possible in very few cases and within very tight limits, e.g. only at very high temperatures. In addition, the precision is frequently not sufficient.

It is known from devices of the applicant, e.g. from the device known by the designation GM35, in gas analyzers which only require a gas passage access at one side, that is which work with a so-called "measuring rod", to provide a pressure and temperature sensor in the measuring rod. Such an integration is, however, not possible when the gas analyzer comprises two units which are arranged opposite one another at the gas line, that is with so-called "cross-duct" devices. The GM35 device of the applicant therefore provides a separate rod for the pressure and temperature measurement for the cross-duct version which would have to be flanged to a separate access.

Starting from this prior art, it is the object of the invention to provide an improved apparatus for the analysis of a fluid with which temperature and/or pressure can also be detected in a simple and in particular in an inexpensive manner.

This object is satisfied by an apparatus having the features of claim 1.

The apparatus in accordance with the invention serves for the analysis of a fluid which is present in a line or in a container. It can e.g. be a gas flow in a gas line. The apparatus has an optoelectronic apparatus for the optical analysis. The optoelectronic apparatus itself includes at least two housing parts having housing flanges for flanging the apparatus to a wall of the line or of the container so that the housing parts are disposed opposite one another, a light transmitter and a light receiver which define an optical measurement path between them within the line or the container and an evaluation device. A temperature sensor for detecting the fluid temperature and/or a pressure sensor for detecting the fluid pressure is/are provided beside the optoelectronic apparatus. Provision is made in accordance with the invention that the fluid temperature or the fluid pressure can be detected in the region of the optical measurement path, for which purpose the temperature measuring apparatus is held extending parallel to the optical measurement path within the line or the container via a spacer or a dynamic pressure pipe of the pressure measuring apparatus and the spacer or the dynamic pressure pipe is fastened to an intermediate flange which can be inserted between one of the housing flanges and the wall.

The invention makes it possible also to provide a temperature and pressure detection in a simple manner with cross-duct devices which is very inexpensive and also allows a retrofitting. No additional "holes" and flanges are required in the region of the measurement point at the gas line. The installation costs are thus above all substantially less expensive. The optical system with which the optical gas analysis takes place, i.e. the optical beam path, is not influenced or is not influenced in a disturbing manner.

Feed lines to a temperature sensors and/or to a pressure sensor are advantageously conducted through the intermediate flange.

To protect the feed lines, they can advantageously be conducted in the spacer.

In a further development of the invention, a connector plug or a connector cable is provided at the intermediate flange for the forwarding of the temperature and pressure signals from the gas passage to the evaluation unit.

The invention will be explained in detail in the following with reference to an embodiment and to the drawing. There are shown in the drawing:

FIG. 1 a schematic representation of an apparatus in accordance with the invention for the analysis of a fluid;

FIG. 2 the apparatus from FIG. 1 along the line I-I.

An apparatus 10 in accordance with the invention for the analysis of a fluid, for example of gas in a gas flow 12 in a flue 13, has an optoelectronic apparatus 14 in an embodiment shown in FIG. 1. It comprises two housing parts 16 and 18. A light transmitter 20, a light receiver 24, a beam splitter 26 and an evaluation device 28 are arranged in the first housing part 16. A retroreflector 30 is arranged in the second housing part 18 which is arranged on the oppositely disposed side of the flue 13. A transmitted light beam 32 transmitted by the light transmitter 20 is received by the light receiver 24 after reflection at the retroreflector 30 and the beam splitter 26. The optical measurement path 33 formed by the light beams 32 includes a measuring volume 34.

The light receiver 24 generates received signals in dependence on the incident light which are evaluated in the evaluation device 24. The optoelectronic apparatus 14 can be used as a transmissiometer therein so that the intensity of the light passing through the measuring volume 34 is measured by the light receiver 24. As a rule, the light transmitter 20 is tuned to a specific wavelength which is absorbed by a gas proportion to be inspected, for example hydrogen sulfide. A statement can then be made via the light received at the light receiver 24 as to how high the concentration of the gas proportion of interest, e.g. of hydrogen sulfide, is in the gas flow 12 which is conducted in the flue 13.

In this embodiment, the transmitter and receiver are arranged in one housing part and the reflector is arranged in the other housing part so that the light passes through the optical measurement path twice. This has the advantage that electric connections are only necessary at one housing part. It would, however, basically also be conceivable that the transmitter is arranged in the first housing part and the receiver is arranged in the second housing part and no reflector is present. The light then only passes through the measurement path once.

A second light receiver 36 can alternatively be arranged in the second housing part 18 and is arranged so that it can, for example, receive scattered light 38 in the forward direction (forward scatter) so that a concentration evaluation of gas proportions or of soot/dust contained can also be carried out in accordance with the principle of scattered light measurement using the optoelectronic apparatus 14. The scattered light 38 taken by the second receiver 36 is evaluated in a second evaluation device 40 for this purpose. The described scattered light receiver can also be integrated in the transmitter unit 16 to measure the scattered light in the backward direction (backward scatter).

The housing parts 16 and 18 each have a housing flange 42 and 44 respectively with which they can be flanged to a contact flange 46 and 48 respectively arranged at a wall of the flue 13.

The apparatus in accordance with the invention furthermore has an intermediate flange 50 which can be flanged in the embodiment shown between the first housing flange 42 and the associated contact flange 46. The intermediate flange 50 serves as a holder for a temperature measuring apparatus 56 and a pressure measuring apparatus 59. The temperature measuring apparatus 56 includes a spacer 52 and a temperature sensor 56. The spacer 52 holds the temperature sensor 56 into the gas flow 12 at its free end to detect the temperature of the gas.

The pressure measuring apparatus 59 includes a dynamic pressure pipe 54 and a pressure sensor 58. The dynamic pressure is detected via the dynamic pressure pipe 54 and is supplied to the membrane of the pressure sensor 58 so that the pressure of the gas can be detected. Generally, other embodiments of the pressure measuring apparatus would also be conceivable. The pressure sensor can thus be mounted outside the intermediate flange to achieve a temperature resistance and only the dynamic pressure pipe extends into the passage. The pressure sensor can, however, also be made so that only the pressure measuring membrane lies in the gas passage and the pressure is forwarded via a transfer medium, e.g. oil, to the outwardly disposed pressure sensor. It would also be conceivable to arrange the pressure sensor directly at the free end of the dynamic pressure pipe 54 if the size of the pressure sensor and its resistance to the conditions in the gas passage of this arrangement permit. The dynamic pressure pipe would then no longer serve for the dynamic pressure, but as a second holder.

The temperature and pressure should be detected as closely as possible to the measurement path so that the values correspond to the values from the optical measurement and a common evaluation is possible. The spacer 52 and the dynamic pressure pipe 54 are therefore aligned substantially parallel to the optical measurement path 33 and their free ends lie in the region of the optical measurement path 33.

The temperature sensor and the pressure sensors 56 and 58 respectively are conducted through the intermediate flange via feed lines 60 and 62, which extend in the spacer 52 and in the pipe 54 respectively, and are ultimately connected to the evaluation device 28 or to a separate evaluation device not shown separately. A connector plug 64 for the corresponding connection to the evaluation unit can be provided outwardly at the intermediate flange 50.

A plan view of the flanges from the inside in the direction of the first housing part 16 is shown in FIG. 2. In this embodiment, the pressure measuring apparatus 59 is disposed in front of the optical measurement path 33 in the direction of flow and the temperature measuring apparatus 57 is disposed behind the optical measurement path 23 in the direction of flow. The gas flow could be disturbed at the site of the optical measurement path 33 in such an arrangement. It can therefore be advantageous to rotate the intermediate flange 50 having the spacers 52 and the dynamic pressure pipe 54 which are attached to it and which are arranged diametrically at the intermediate flange 50 in this embodiment, by 90° for example. The temperature and pressure measurement apparatus would then lie next to the optical measurement path viewed in the flow direction and would effect a smaller disturbance of the gas flow at the site of the optical measurement path.

The invention claimed is:

1. An apparatus for the analysis of a fluid in a line (13) or in a container, having an optoelectronic apparatus (14) for the optical analysis, comprising:
    at least two housing parts (16, 18) having housing flanges (42, 44) for flanging to a wall of the line (13) or of the container so that the housing parts are disposed opposite one another;
    a light transmitter (22) and a light receiver (24) which define an optical measurement path (33) between them within the line (13) or the container;
    and an evaluation unit (28),
    further having a temperature measurement apparatus (57) and/or a pressure measuring apparatus (59), wherein, for detecting the fluid temperature or fluid pressure in the region of the optical measurement path (33), the temperature measuring apparatus (57) is held extending parallel to the optical measurement path (33) within the line (13) or the container via a spacer (52) or a dynamic pressure pipe (54) of the pressure measuring apparatus (59) and the spacer (52) or the dynamic pressure pipe (54) is fastened to an intermediate flange (50) which can be inserted between one of the housing flanges (42 and 44 respectively) and the wall.

2. An apparatus in accordance with claim 1, wherein the feed lines (60, 62) are conducted to a temperature sensor (56) of the temperature measurement apparatus (57) or to a pressure sensor (58) of the pressure measurement apparatus (59) by the intermediate flange (50).

3. An apparatus in accordance with claim 2, wherein the feed lines (60) are conducted to the temperature sensor (56) into the spacer (52).

4. An apparatus in accordance with claim 2, wherein the intermediate flange (50) has connector plugs (60) for connecting the feed lines (60, 62) to the evaluation unit (28).

5. An apparatus in accordance with claim 3, wherein the intermediate flange (50) has connector plugs (60) for connecting the feed lines (60, 62) to the evaluation unit (28).

* * * * *